(12) United States Patent
Michon et al.

(10) Patent No.: US 6,248,570 B1
(45) Date of Patent: Jun. 19, 2001

(54) PROCEDURES FOR THE EXTRACTION AND ISOLATION OF BACTERIAL CAPSULAR POLYSACCHARIDES FOR USE AS VACCINES OR LINKED TO PROTEINS AS CONJUGATE VACCINES

(75) Inventors: Francis Michon, Bethesda; Milan Blake, Fulton, both of MD (US)

(73) Assignee: Baxter International, Inc., Deerfield, IL (US)

(*) Notice: Subject to any disclaimer, the term of this patent is extended or adjusted under 35 U.S.C. 154(b) by 0 days.

(21) Appl. No.: 09/221,630

(22) Filed: Dec. 23, 1998

Related U.S. Application Data

(60) Provisional application No. 60/068,608, filed on Dec. 23, 1997.

(51) Int. Cl.[7] .............................. C12P 19/04; C08B 37/00
(52) U.S. Cl. .................. 435/101; 435/253.4; 536/127; 536/123; 424/244.1; 424/234.1
(58) Field of Search ................. 435/101, 253.4; 536/127, 123; 424/244.1, 234.1, 250.1

(56) References Cited

U.S. PATENT DOCUMENTS

| | | | |
|---|---|---|---|
| 3,577,527 | * 5/1971 | Edwards | 424/250.1 |
| 4,356,170 | * 10/1982 | Jennings et al. | 424/92 |
| 4,413,057 | 11/1983 | Carlo et al. | |
| 5,190,746 | 3/1993 | Cassels et al. | |

FOREIGN PATENT DOCUMENTS

| | | |
|---|---|---|
| 0238739 | 9/1987 | (EP). |
| 1107693 | 3/1968 | (GB). |

OTHER PUBLICATIONS

Schifferle et al, J. Immunol. 135(6): 4164–4170, 1985.*
von Hunolstein, C., L. Nicolini, S. D'Ascenzi, C. Volpe, G. Alfarone and G. Orefici. "Sialic acid and biomass production by Streptococcus agalactiae under different growth conditions" Appl.Microbiol.Botechol. 38:458–462, 1993.

Wessels, M.R., J.L. DiFabio, V.J. Benedi, et al., Structural determination and immunochemical characterization of the type V group B Streptococcus capsular polysaccharide. J.Biol.Chem. 266:6714–6719, 1991.

Wessels, M.R., W.J., Benedi, H.J., Jennings, F. Michon, J.L. DiFabio and D.L. Kasper., Isolation and characterization of type IV group B Stretococcus capsular polysaccharide. Infect.Immun. 57:1089–1094, 1989.

Jennings, H.J. K.G. Rosell, E. Katzenellenbogen and D.L. Kasper Structural determination of the capsular polysaccharide antigen of type II Group B Streptococcus. J.Biol.Chem. 258:1793–1798, 1983.

Jennings, H.J., E. Katzenellenbogen, C. Lugowski and D.L. Kasper, Structure of the native polysaccharide antigens of type Ia and type Ib Group B Streptococcus. Biochemistry 22:1258–1263, 1983.

Jennings, H.J., K.G., Rosell and D.L. Kasper, Structural determination and serology of the native polysaccharide antigen of type III group B Streptococcus. Can.J. Biochem. 58:112–120, 1980.

Jennings, H.J., K.G., Rosell and D.L. Kasper, Structure and serology of the native polysaccharide antigen of type Ia group B Streptococcus. Proc.Nat.Acad.Sci. USA. 77:2931–2935, 1980.

\* cited by examiner

Primary Examiner—Francisco Prats
(74) Attorney, Agent, or Firm—Morgan & Finnegan, L.L.P.

(57) ABSTRACT

A procedure to isolate large quantities of capsular poly saccharides (CPS) from culture supernatants as well as bacterial cells of gram-negative and gram-positive bacteria using base extraction is described. The procedure is simple, rapid, reproducible and applicable to a variety of bacterial species. The method also yields novel CPS characterized by their lack of covalent attachment to extraneous peptidoglycan. Vaccines and methods of immunization against bacterial infection using the CPS obtained by the process of the invention are also disclosed.

40 Claims, 12 Drawing Sheets

Inhibtion of Rabbit Anti-GBSPV-TT Antiserum on GBSPV-HSA Coated Plate

FIGURE 10

PROCEDURES FOR THE EXTRACTION AND ISOLATION OF BACTERIAL CAPSULAR POLYSACCHARIDES FOR USE AS VACCINES OR LINKED TO PROTEINS AS CONJUGATE VACCINES

Priority is claimed from U.S. Provisional Application Ser. No. 60/068,608 filed Dec. 23, 1997 which is incorporated herein by reference.

FIELD OF THE INVENTION

The present invention relates to methods for extracting and isolating capsular polysaccharides (CPS) from both gram-negative and gram-positive bacteria. The extracted polysaccharides are useful for producing vaccines comprising the polysaccharides alone or conjugated to proteins.

BACKGROUND OF THE INVENTION

Bacterial infections caused by gram-positive bacteria such as Streptococcus, Staphylococcus, Enterococcus, Bacillus, Corynebacterium, Listeria, Erysipelothrix, and Clostridium and by gram-negative bacteria such as Haemophilus, Shigella, *Vibrio cholerae*, Neisseria and certain types of *Escherichia coli* cause serious morbidity throughout the world. This, coupled with the emerging resistance shown by bacteria to antibiotics, indicates the need for the development of bacterial vaccines. For example, streptococci are a large and varied genus of gram-positive bacteria which have been ordered into several groups based on the antigenicity and structure of their cell wall polysaccharide (26, 27). Two of these groups have been associated with serious human infections. The group A streptococci cause a variety of infectious disorders including "strep throat", rheumatic fever, streptococcal impetigo, and sepsis.

Group B streptococci were not known as human pathogens in standard medical textbooks until the early 1970's. Since that time, studies have shown that group B streptococci are important perinatal pathogens in the United States as well as developing countries (37). Systemic group B streptococcal infections during the first two months of life affect approximately three out of every 1000 births (12), resulting in 11,000 cases annually in the United States. These infections cause symptoms of congenital pneumonia, sepsis, and meningitis. A substantial number of these infants die or have permanent neurological sequelae. Furthermore, group B streptococcal infections may be implicated in the high pregnancy-related morbidity which occurs in nearly 50,000 women annually. Others at risk from group B streptococcal infections are those who have an altered immune response, either congenitally, chemotherapeutically, or by other means.

Group B streptococci can be further classified into several different types based on the bacteria's capsular polysaccharide. Types Ia, Ib, II, III, IV, V, VI, VII, and VIII account for most of the pathogenicity due to group B infection, with group B streptococci types Ia, Ib, II, III, and V representing over 90% of all reported cases. The structure of each of these various type polysaccharides has been characterized (19–22, 44). Similar to findings with many other human bacterial pathogens, capsular polysaccharides of group B streptococci, when used in vaccines, may provide effective protection against infections with these bacteria. See 4, 6, 24, 29, 30, 42, 43, 45.

Gram-negative bacteria are also a significant cause of disease. Until the recent development and use of polysaccharide-proteinvaccines directed against Haemophilus influenzae type b bacteria (Hib), Hib bacterial infections were responsible for many cases of mental retardation in infants. N. menigitidis and *E. coli* K1 infections are responsible for neonatal meningitis. Strains of gram-negative bacteria, *E. coli*, have been linked to serious illness including death from eating meat tainted with *E. coli* strains.

Large-scale production of capsular polysaccharide vaccines, and capsular polysaccharide conjugate vaccines, requires adequate supplies of purified capsular polysaccharides. Prior art methods (40, 42) for isolating capsular polysaccharides from bacterial cells rely on treatment of cells with the enzyme mutanolysin. Mutanolysin cleaves the bacterial cell wall which frees the cellular components. This procedure involves treating cell lysates with additional enzymes to remove proteins and nucleic acids and purification by differential precipitation and chromatography. More efficient, higher yielding and simpler means of obtaining purified capsular polysaccharides are desirable.

SUMMARY OF THE INVENTION

This invention provides a method for extracting capsular polysaccharides (CPS) from the cellular components of both gram-negative and gram-positive bacteria. The CPS can be extracted according to this invention from either bacterial supernatants or bacterial cells by hydrolysis of the base labile bond that connects the CPS to other cellular components. An advantage of the extraction procedure provided by this invention is that the extracted CPS are largely intact.

Another embodiment of this invention provides a method for obtaining purified capsular polysaccharide by deacetylating a percentage of the N-acetyl groups of the CPS during base extraction to facilitate separation of the CPS from other cellular components. A percentage of the acetyl groups can be reintroduced to afford purified CPS having the same repeat unit structure with respect to the N-acetyl groups as native polysaccharide, or, alternatively, acylation with modified alkyl groups can be used to obtain modified CPS.

In a preferred embodiment, the CPS are extracted from group B streptococci (GBS). In a most preferred embodiment the CPS are extracted from GBS types Ia, Ib, II, III, V and VIII.

In another preferred embodiment, the CPS are extracted from *S. pneumoniae*. In a most preferred embodiment the CPS are extracted from *S. pneumoniae* types III, IV and XIV.

In another preferred embodiment, the CPS are extracted from Neisseria or Escherichia bacteria. In a most preferred embodiment the CPS are extracted from *Neisseria meningitidis* types B, C, Y or W135 or *Escherichia coli* K1.

Purification of capsular polysaccharides from either bacterial supernatants or bacterial cells according to this invention has the following advantages over other methods: (a) simplicity (a minimal number of steps), (b) efficiency (high yield and purity), (c) safety (e.g., reduction or elimination of the use of flammable organic solvents), and (d) general applicability to all gram-negative and gram-positive bacteria.

The method according to the invention comprises treatment of a concentrated extract and/or isolated bacterial cells with a basic solution. In addition to extracting the CPS, the base extraction also causes deacetylation of N-acetyl groups. The extent of the deacetylation may be varied by adjusting the reaction conditions. The extracted CPS are then separated from the cellular components to obtain the CPS preferably by chromatographic separation. Some or most of the acetyl groups may be reintroduced to obtain CPS or modified CPS. Final purification of the CPS may be achieved by gel-permeation chromatography. In a further embodiment, the invention provides novel, optionally modified CPS as a result of the basic extraction conditions which are suitable for use as vaccines or conjugate vaccines.

It is an embodiment of this invention to provide a method for producing substantially pure CPS which are capable of eliciting the production in mammals of antibodies that are bactericidal and protect the animals against infection.

It is another embodiment of this invention to use these CPS in vaccines, either alone or conjugated to a polypeptide, to protect humans or animals against infection, typically by that strain of bacteria from which the CPS was isolated. In certain cases the polysaccharide used with this invention may induce production of antibodies which are cross-reactive with other pathogenic bacteria thereby producing protection against infection by these other bacteria.

It is an objective of this invention to provide a method for isolating capsular polysaccharides from both gram-negative and gram-positive cellular components contained in either gram-negative or gram-positive bacterial supemates or gram-negative or gram-positive bacterial cells. These capsular polysaccharides can then be used as vaccines or bound to polypeptides to form conjugate molecules which are useful as vaccines.

BRIEF DESCRIPTION OF THE DRAWINGS

FIG. 10: Inhibition of rabbit anti-GBSPV-TT antiserum on GBSPV-HAS coated plates.

DETAILED DESCRIPTION OF THE INVENTION

Figure 1:
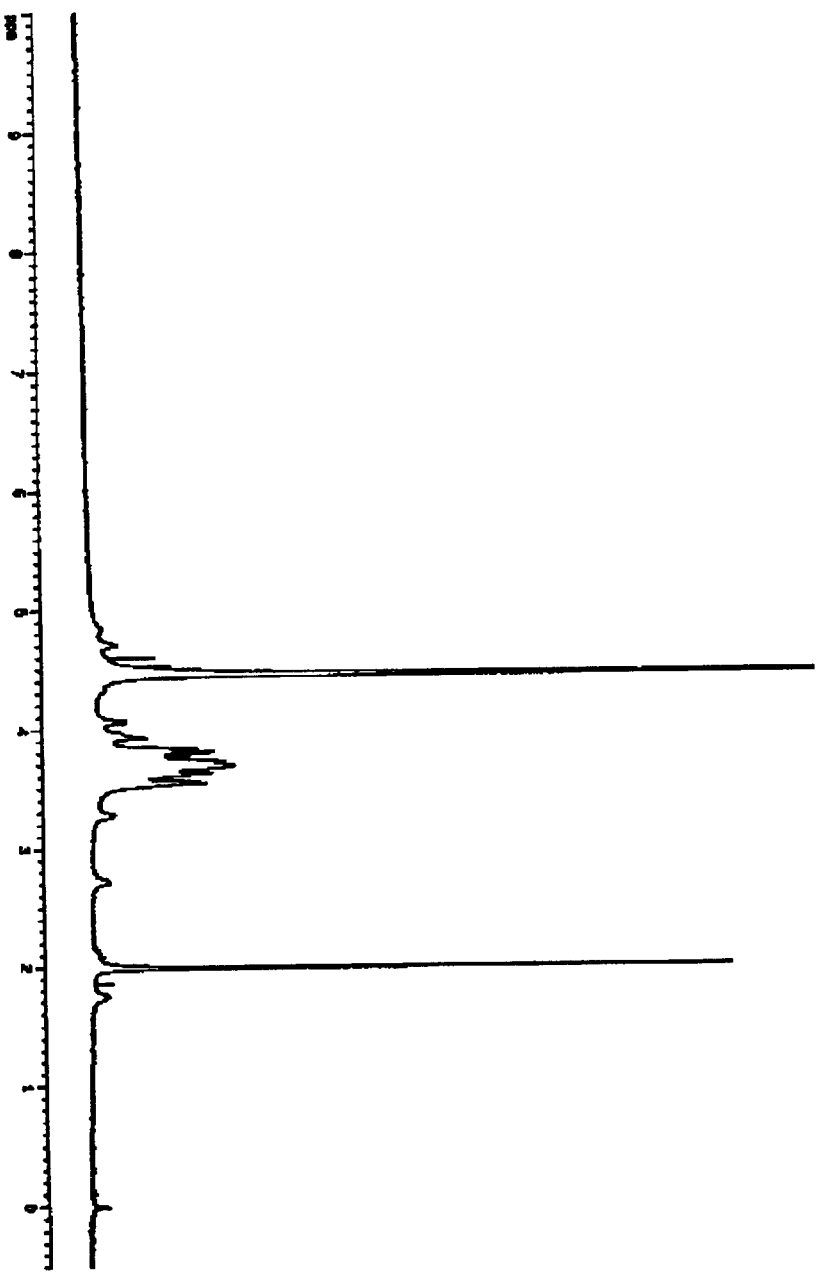
FIG. 1: NMR spectrum (500 MHz) of the capsular polysaccharide obtained from group B Streptococci type Ia recorded in $D_2O$ at 50° C.
Figure 2:
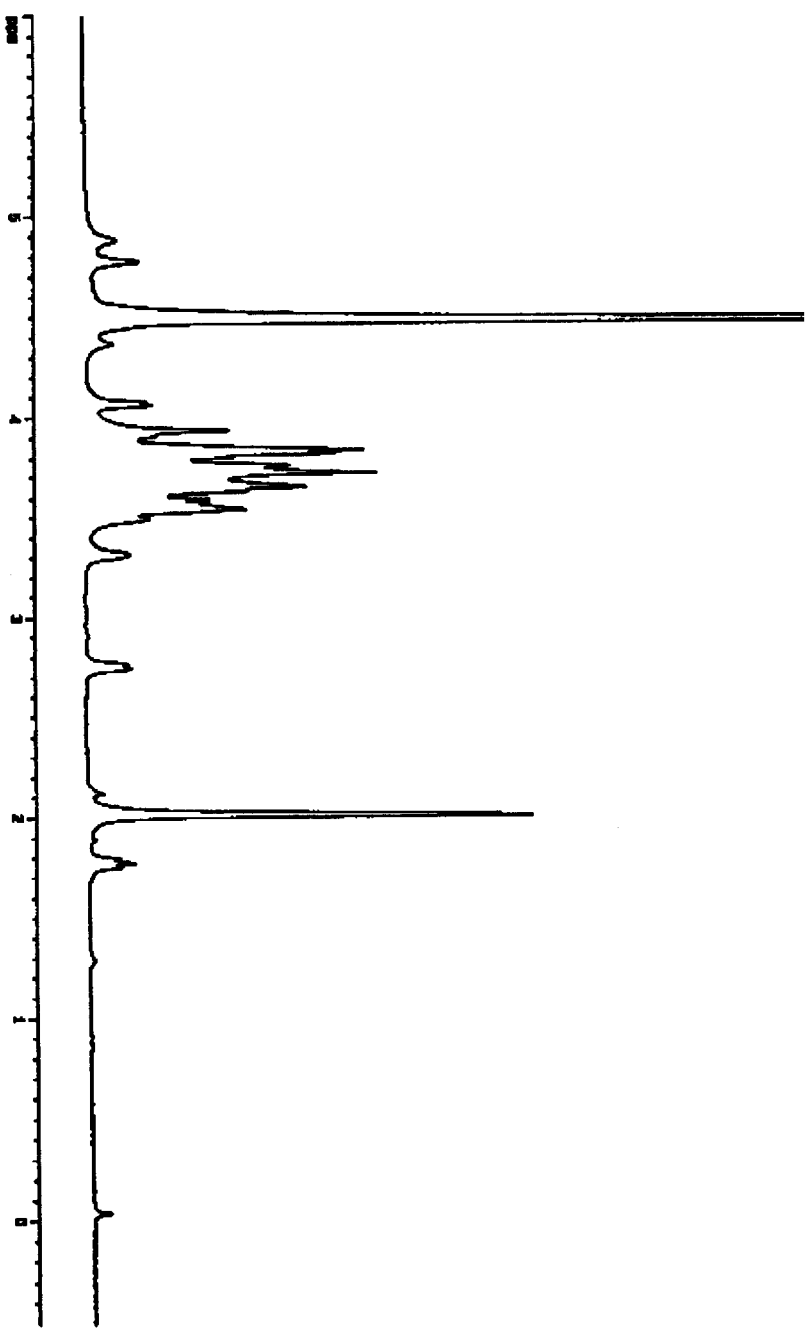
FIG. 2: NMR spectrum (500 MHz) of the capsular polysaccharide obtained from group B Streptococci type Ib recorded in $D_2O$ at 50° C.
Figure 3:
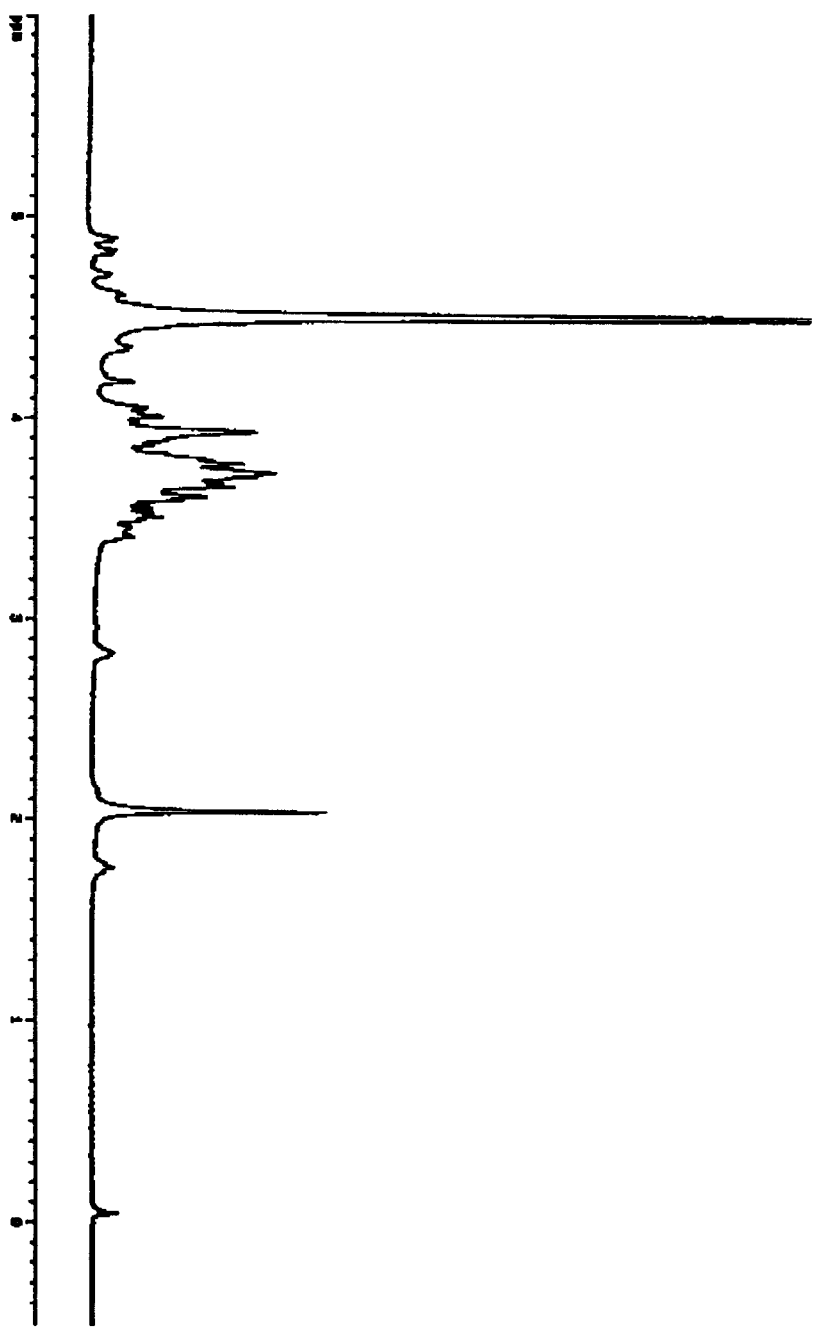
FIG. 3: NMR spectrum (500 MHz) of the capsular polysaccharide obtained from group B Streptococci type II recorded in $D_2O$ at 50° C.
Figure 4:
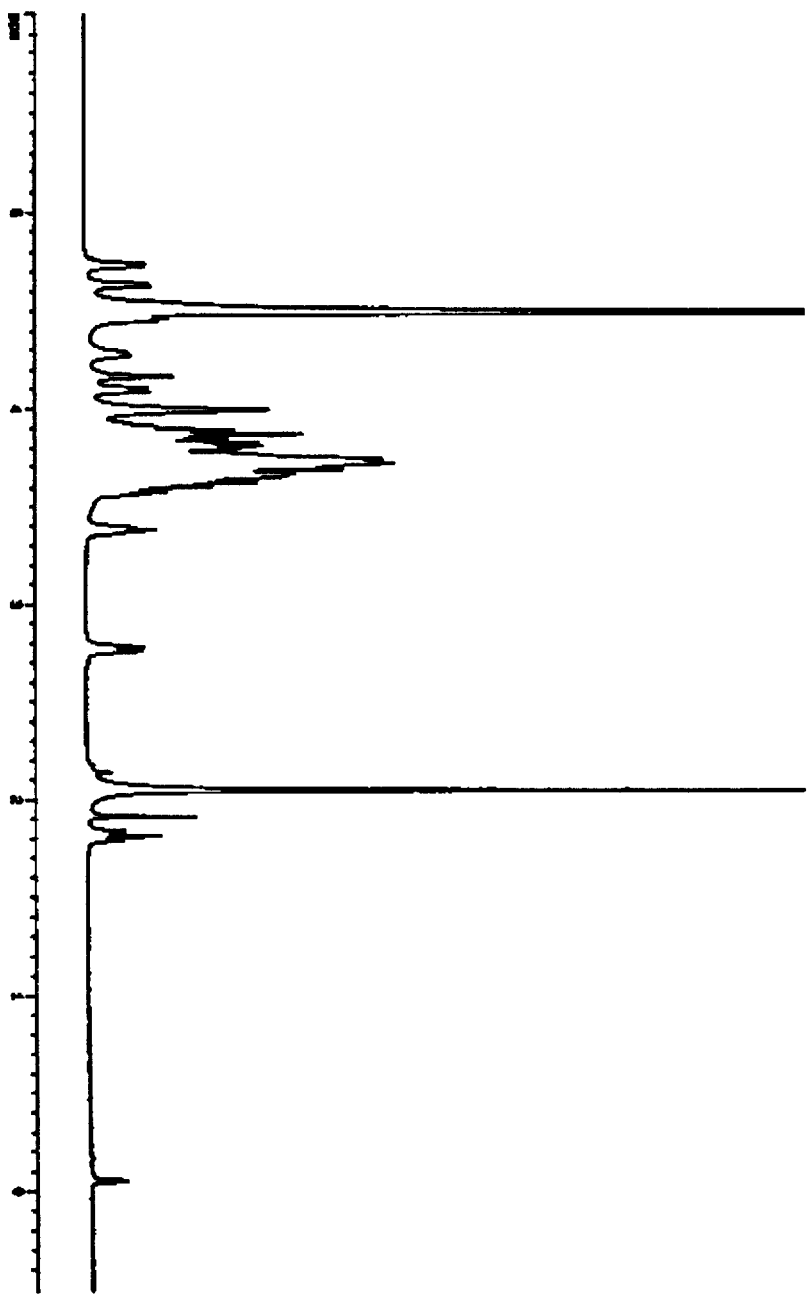
FIG. 4: NMR spectrum (500 MHz) of the capsular polysaccharide obtained from group B Streptococci type III recorded in $D_2O$ at 50° C.
Figure 5:
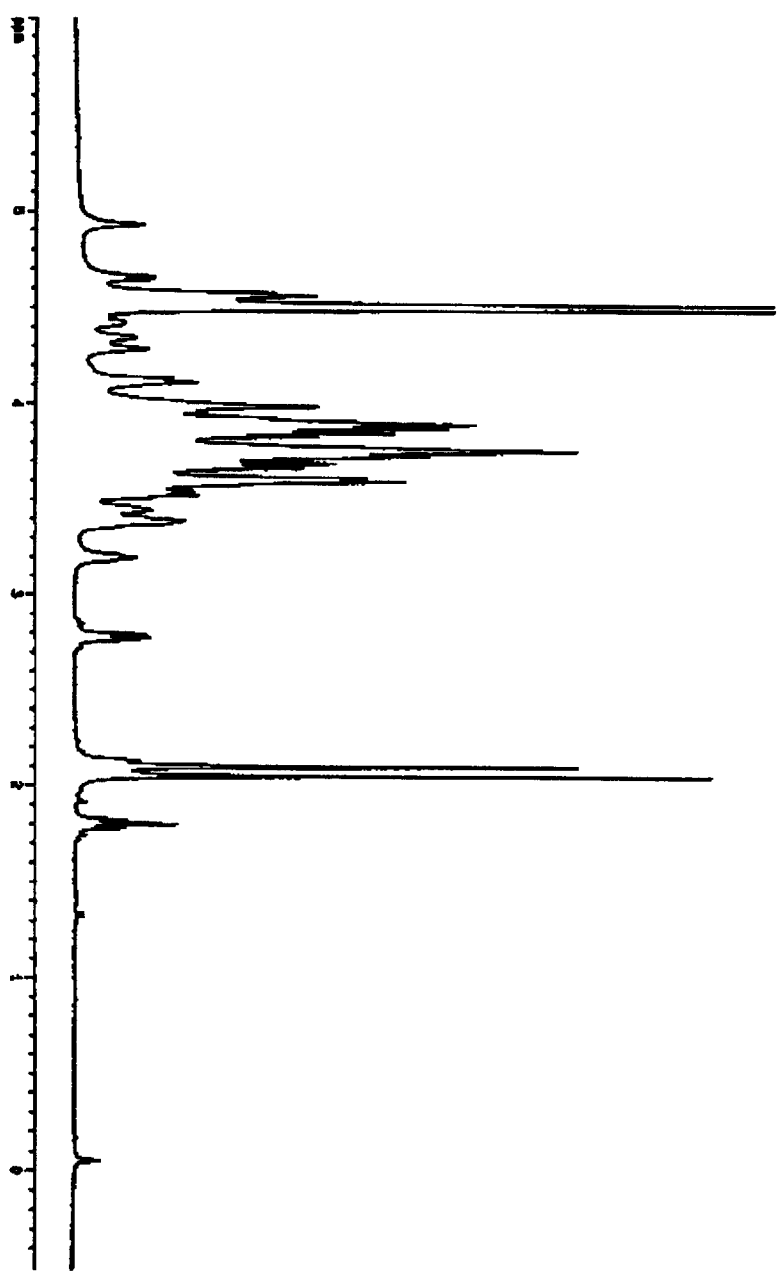
FIG. 5: NMR spectrum (500 MHz) of the capsular polysaccharide obtained from group B Streptococci type V recorded in $D_2O$ at 50° C.
Figure 6:
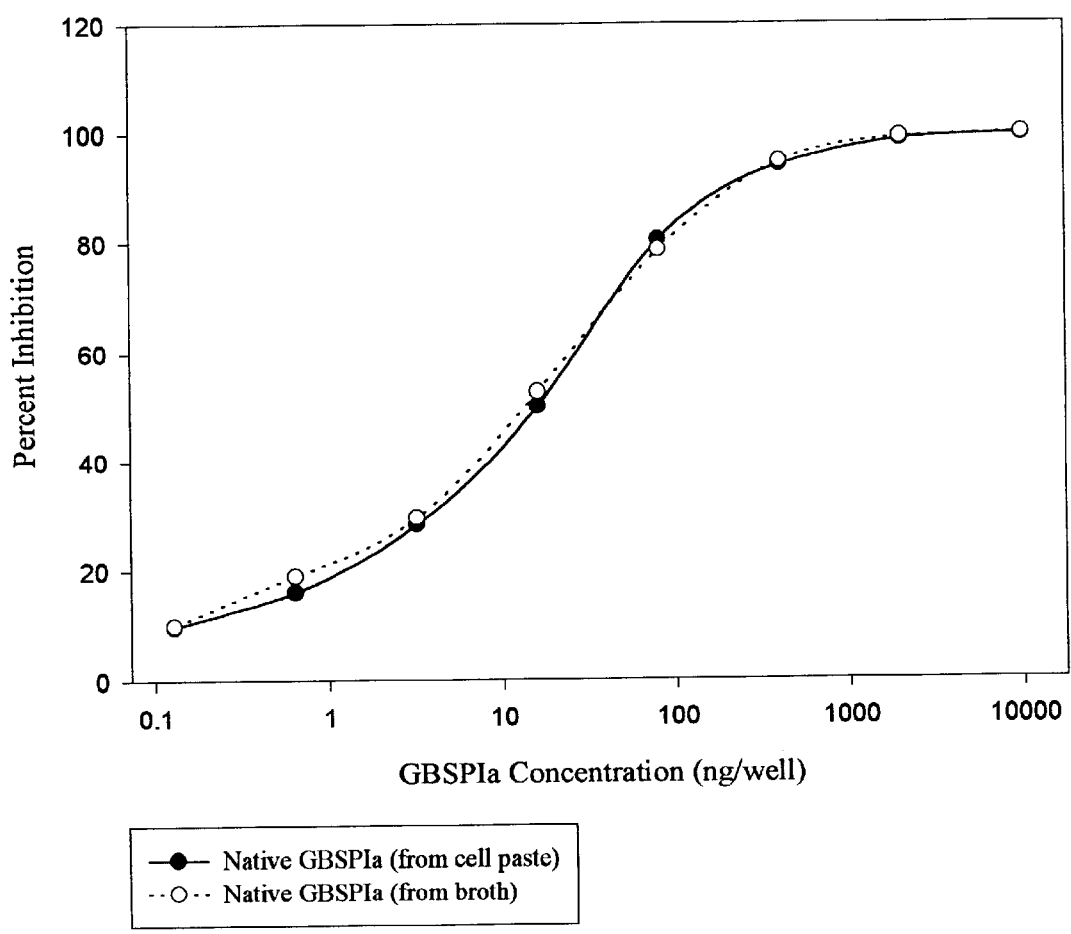
FIG. 6: Inhibition of rabbit anti-GBSPIa antiserum on GBSPIa-HSA coated plates.
Figure 7:
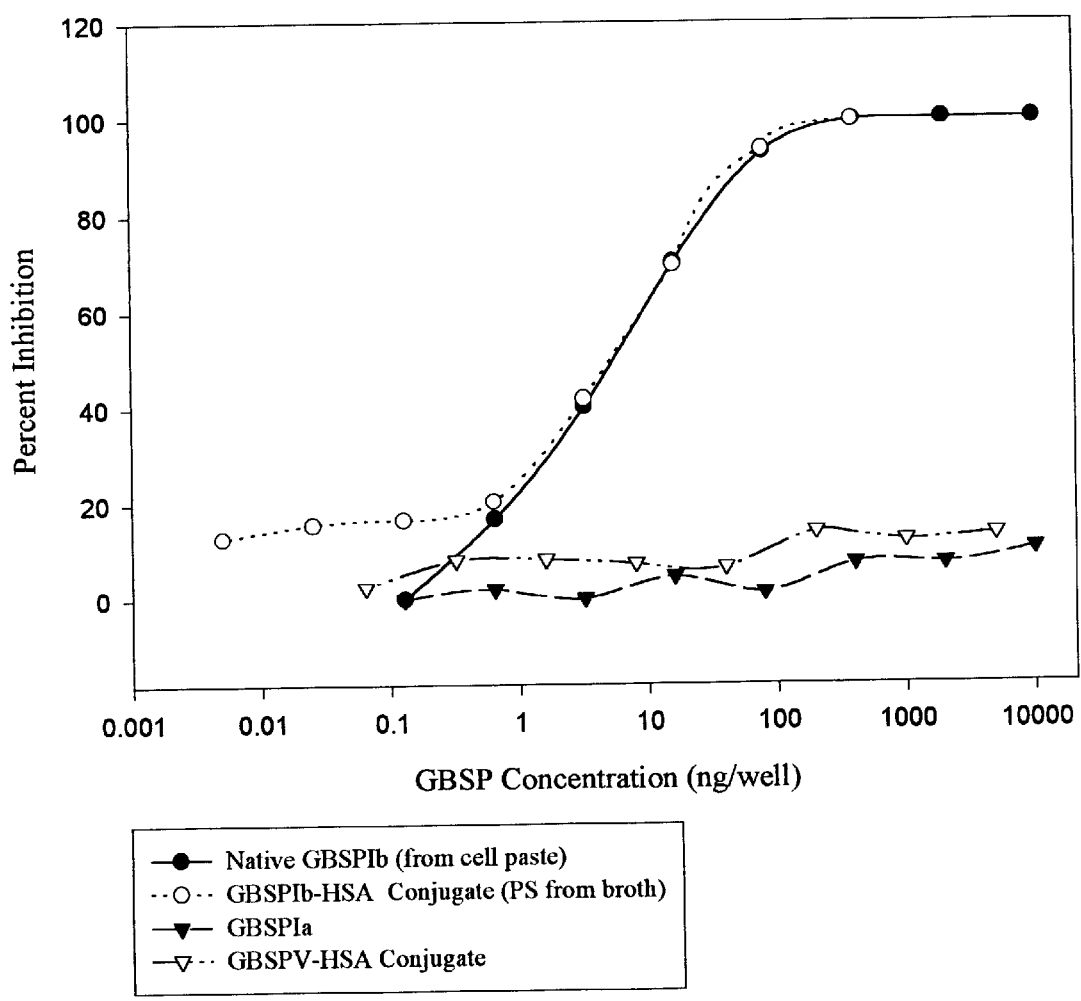
FIG. 7: Inhibition of rabbit anti-GBSPIb antiserum on GBSPIb-HSA coated plates.
Figure 8:
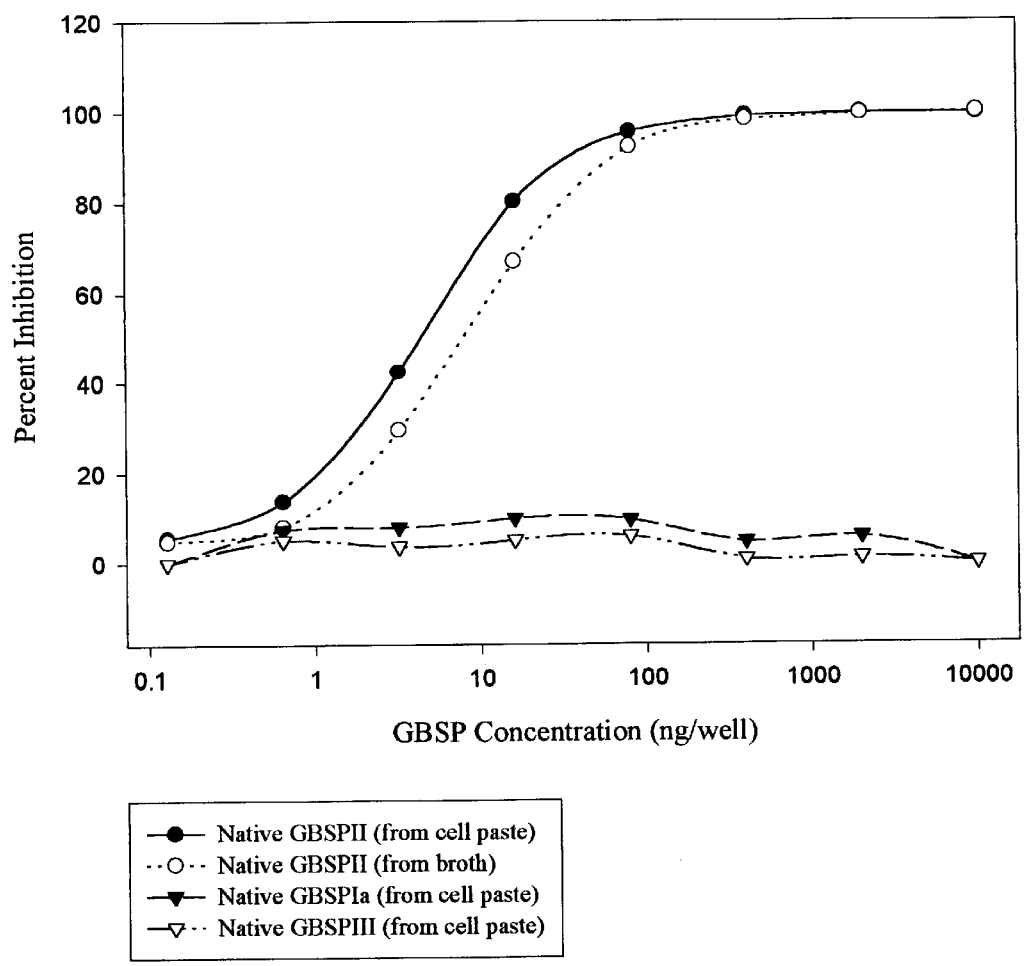
FIG. 8: Inhibition of rabbit anti-GBSPII antiserum on GBSPII-HSA coated plates.
Figure 9:
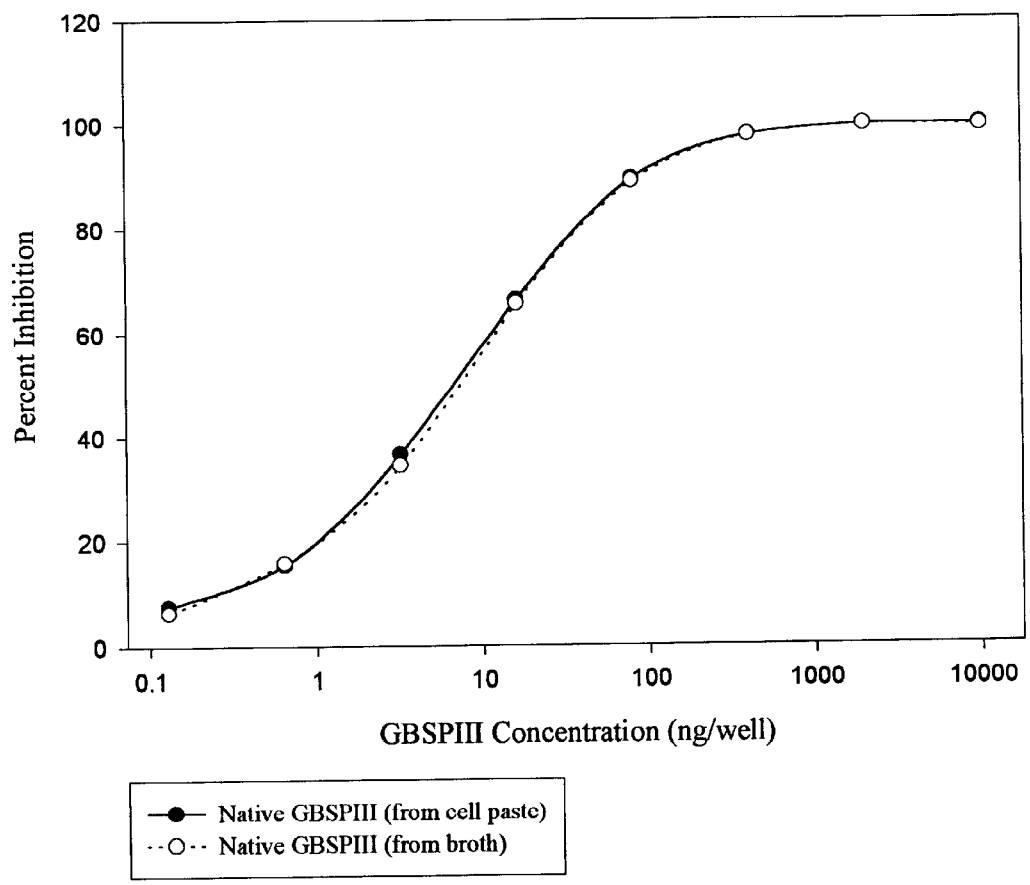
FIG. 9: Inhibition of rabbit anti-GBSPIII antiserum on GBSPIII-HSA coated plates.

This invention provides a method for obtaining capsular polysaccharides from gram-negative and gram-positive bacteria by using base hydrolysis of the base-labile bond that attaches the CPS to the cellular components. The method of the invention comprises extracting CPS of both gram-positive and gram-negative bacteria by contacting bacteria or a solution containing bacteria fragments with a base. CPS may then be recovered from the base by a variety of methods. Non-limiting examples of gram-positive bacteria for use according to this invention are Streptococci, Staphylococci, Enterococci, Bacillus, Corynebacterium, Listeria, Erysipelothrix, and Clostridium. Specifically, the use of Streptococci is more preferred and the use of group B streptococci types Ia, Ib, II, III, IV, V, VI, VII and VIII is most preferred. Non-limiting examples of gram-negative bacteria for use with this invention include *Haemophilus influenzae, Neisseria meningitidis* and *Escherichia coli*. Specifically, the use of *H. influenzae* type b, N. meningitidis types B, C, Y and W135 and *E. coli* K1 are more preferred.

A wide variety of conditions can be used to hydrolyze the base-labile bond in either aqueous or organic solvent according to the invention. The extent to which N-acetyl bonds of the carbohydrates are also hydrolyzed can be controlled by the reaction conditions. The hydrolysis of the N-acetyl groups is advantageous for separating the CPS from the other cellular components because the greater extent to which the N-acetyl bonds are cleaved, the more hydrophilic, relative to the rest of the cellular components, the CPS becomes. This difference in polarity can be exploited to effect an efficient chromatographic separation. The separation of two or more components of a mixture based on differences in polarity is well known to those skilled in the art.

For example, using hydrophobic-interaction chromatography, compounds of relatively greater hydrophobicity are retained longer on the column relative to those compounds that are more hydrophilic. Conversely, using hydrophilic-interaction chromatography, hydrophilic compounds are retained longer on the column relative to those compounds that are more hydrophobic. Using both methods consecutively allows for the removal of impurities that are both less polar and more polar relative to the compound of interest.

Alternatively, free amino or carboxylic acid groups present on the CPS can be exploited to facilitate an efficient chromatographic separation. The separation of two or more components of a mixture based on differences in charge is well known to those skilled in the art. Using cation exchange chromatography, compounds which contain positively charged groups such as protonated amines are retained longer on the column than those compounds that have little or no positive charge pass which pass through the column relatively quickly. Conversely, using anion exchange chromatography, negatively charged compounds such as carboxylic acids are retained on the column while those compounds that have little or no negative charge pass through the column relatively quickly.

After separating the deacetylated CPS from the other cellular components, the free amino groups can be reacetylated. Varying the acetylating reagent and reaction conditions allows the practitioner to control the extent to which the amino groups are reacetylated. The impurities introduced in the acylation step are small in size in comparison to the reacylated CPS and may therefore be separated from the CPS by gel-permeation chromatography.

For example, gel-permeation chromatography allows for efficient separation of the relatively large CPS. Alternatively, the difference in polarity or charge can be exploited to purify the CPS from the remaining impurities.

A. Preparation of capsular polysaccharides

Isolation and purification of bacterial polysaccharides from cellular components can be, according to the invention, achieved in four steps: base extraction, chromatographic separation, N-acylation, and chromatographic purification.

1. Starting Materials

Materials for extracting CPS can be obtained from concentrated bacterial supernatants from homogenized bacterial cells or conditioned medium. Cells may be separated by centrifugation or microfiltration and the supernate concentrated, typically 10–15 fold. Preferably the bacterial supernatants and conditioned medium are concentrated so that the CPS are present at a concentration of about 5–20 mg/ml. In addition, pelleted cells can be extracted directly.

2. Base extraction

The concentrated bacterial supernatant or conditioned medium can be contacted with a variety of bases to extract the CPS. Alternatively, isolated bacterial cells can be further contacted with a variety of bases to extract the CPS. Non-limiting examples of bases which may be used according to this invention are NaOH, KOH, LiOH, NaHCO$_3$, Na$_2$CO$_3$, K$_2$CO$_3$, KCN, Et$_3$N, NH$_3$, H$_2$N$_2$H$_2$, NaH, NaOMe, NaOEt or KOtBu. Bases such as NaOH, KOH, LiOH, NaH, NaOMe or KOtBu are most effectively used in a range of 0.5 N–5.0 N. Bases such as NaHCO$_3$, Na$_2$CO$_3$, K$_2$CO$_3$ and KCN can be used in concentrations as high as their solubilities permit. Organic bases such as Et$_3$N can be used at medium to high (50–100%) concentrations as long as there is an agent such as water or alcohol to effect the hydrolysis. Bases such as NH$_3$ or H$_2$N$_2$H$_2$ can be used at nearly any concentration including 100%. Solvents such as water, alcohols (preferably C$_1$–C$_4$), dimethylsulfoxide, dimethylformamide or mixtures of these and other organic solvents can be used. Base extraction solutions comprising water are most preferred.

The most effective pH range for extracting the CPS from the cellular components is from about 9 to 14 with the optimal pH being around 12. Although extraction may be accomplished at temperatures from about 4° C., increasing the temperature to preferably between about 40 to 100° C. and/or agitation of the reaction mixture is expected to result in increased yields. It is preferred to use approximately 1–20 g of cells paste to about 1 liter of base reagent. Alternatively, the concentrated supernatants are diluted with 10 N NaOH to a final concentration of 2 N NaOH in the reaction mixture.

3. Chromatographic separation

The extracted CPS present in the base extraction reagent can be separated from impurities resulting from the cellular components by chromatography. Non-limiting examples of the chromatographic separation methods are ion-exchange (cationic or anionic), hydrophilic-interaction, hydrophobic-interaction or gel-permeation chromatography. The preferred method is hydrophobic-interaction chromatography (HIC). More preferred is hydrophobic-interaction chromatography on phenyl sepharose which will remove most of the high-molecular-weight, uv-active contaminants from the base extract. Capsular polysaccharide will elute in the beginning of the high-pH (pH 10 to pH 8), high-salt (2 N to 1 N) elution, while the more hydrophobic protein and nucleic acids will be retained. Non-limiting examples of the hydrophobic-interaction chromatographic method are alkyl agarose or sepharose resins with Phenyl Sepharose HP (Pharmacia Biotech; Piscataway, N.J.) being a preferred resin. The column can be pre-equilibrated with from 0.5–5.0 N NaHCO$_3$ and eluted with one column volume at a flow rate from 0.5–50 ml/min. After eluting with about one column volume of NaHCO$_3$ about one to ten column volumes of water can be used to elute the column. Fractions can then be assayed for polysaccharide by means known to those skilled in the art. A preferred method for the detection of polysaccharide containing sialic acid is a microscale orcinol assay described in the Examples.

4. N-Acetylation

Separation of extracted capsular polysaccharide under basic conditions is aided by the removal during extraction of N-acetyl groups from sialic acid and aminosugar residues of the otherwise base-stable capsular polysaccharides.

The pooled HIC fractions containing the capsular polysaccharides optionally can be reacetylated to the extent desired by using a variety of acetylating agents. Non-limiting examples of acetylating agents are acetic anhydride, acetyl chloride, pentafluorophenyl acetate, 4-nitrophenyl acetate. See: Theodora W. Greene and Peter G. M. Wuts, *Protective Groups in Organic Syntheses*, 2nd Ed. (1991). The preferred method is mixing with acetic anhydride, at concentrations from about 0.5 M to about 2 M with preferred concentrations from about 0.7 M to about 1 M, to reacetylate the capsular polysaccharide's free amino groups, thus regenerating the native polysaccharide structure.

5. Chromatographic purification

Purification of re-acetylated CPS may then be accomplished to yield CPS for use in preparing immunological reagents such as antigens, and vaccines. Various examples of chromatographic purification are suitable for use with this invention. For example, ion-exchange (cationic or anionic), hydrophobic-interaction, hydrophilic-interaction, or gel-permeation chromatography may all be used to effect separation of the re-acetylated CPS from reaction components. The preferred method is the use of gel-permeation chromatography on Superdex (cross-linked agarose and dextran) which will remove residual contaminants and afford purified CPS. Particularly preferred is Superdex 200 PG which has a fractionation range (MW) for dextrans of 1,000–100,000. Flow rates are preferably from about 0.1 to 10 ml/min using PBS as eluant.

Figure 11:
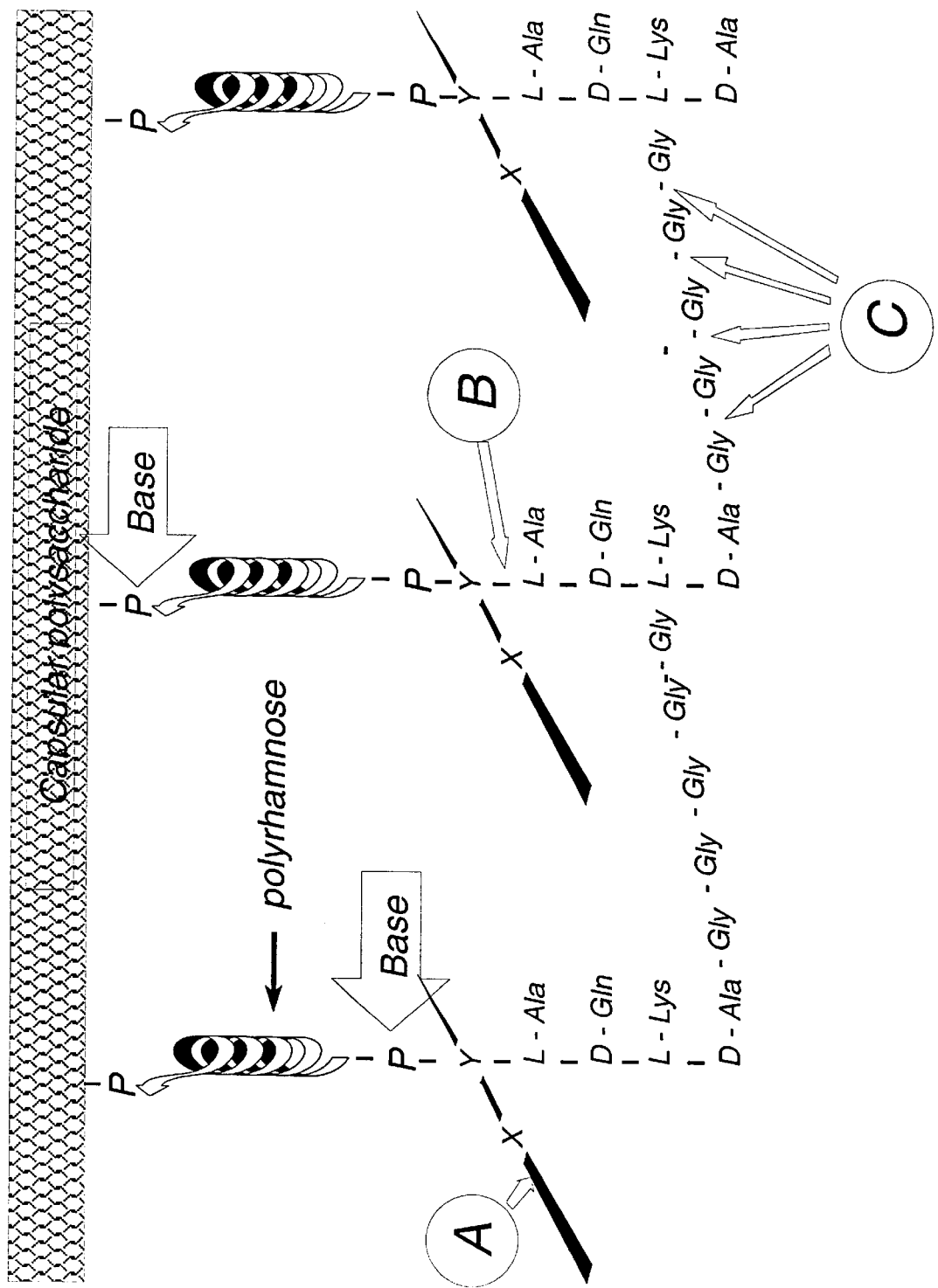
FIG. 11: GBS structural assembly depicting peptidoglycan together with group subcapsular antigen (polyrhamnose) and capsular polysaccharide (Michon et al., *Biochemistry* 1988, 27:5341–5351). X and Y represent residues of N-acetylglucosamine and N-acetylmuramic acid respectively. Open arrows indicate the predicted cleavage sites by: lysozyme (A), mutanolysin (B), lysostaphin (C) or base by hydrolysis of phosphodiester bonds linking the capsular polysaccharide and the polyrhamnose to the peptidoglycan.
Figure 12:
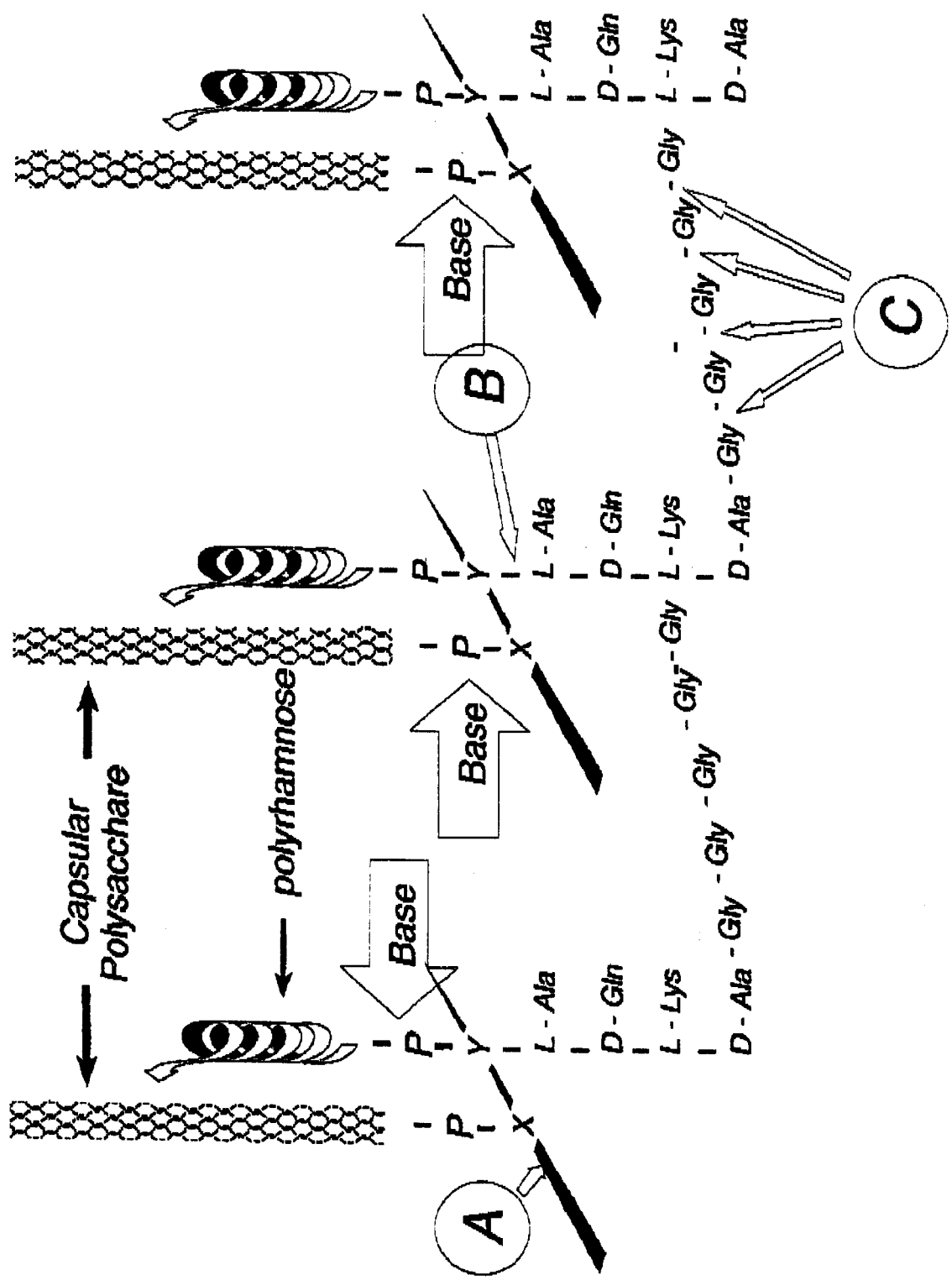
FIG. 12: GBS structural assembly depicting peptidoglycan together with group subcapsular antigen (polyrhamnose) and capsular polysaccharide (Michon et al., *Biochemistry* 1988, 27:5341–5351). X and Y represent residues of N-acetylglucosamine and N-acetylmuramic acid respectively. Open arrows indicate the predicted cleavage sites by: lysozyme (A), mutanolysin (B), lysostaphin (C) or base by hydrolysis of phosphodiester bonds linking the capsular polysaccharide to the peptidoglycan and by hydrolysis of phosphodiester bonds linking the polyrhamnose to the peptidoglycan.

The capsular polysaccharides produced by the base extraction methods of this invention are novel (see FIGS. 11 and 12) and maintain epitopes on their native structures (FIGS. 5–10). Accordingly, the CPS prepared according to the invention elicit production of antibodies which are cross-reactive with native CPS and bacteria expressing them. Obtaining CPS by methods according to this invention is superior to methods of the prior art because of (a) the relative ease with which the methods of this invention are carried out, (b) increased yields of isolation and (c) increased yields for conjugation. In addition, bacterial DNA and RNA are degraded in the base extraction step and therefore are not present in appreciable amounts in the final product produced according to this invention.

B. Structure of extracted CPS

The capsular polysaccharides extracted by the method of this invention have a unique structure compared to CPS extracted by prior methods. The CPS are obtained by base catalyzed hydrolysis of phosphodiester bonds linking the capsular polysaccharides to polyrhamnose and by base catalyzed hydrolysis of phosphodiester bonds linking the polyrhamnose to peptidoglycan (see FIG. 11). According to an alternative model for the bacterial cell wall structure, the same structurally unique CPS are obtained by base catalyzed hydrolysis of phosphodiester bonds linking the capsular polysaccharides to the peptidoglycan and by base catalyzed hydrolysis of phosphodiester bonds linking polyrhamnose to the peptidoglycan (see FIG. 12). Methods of prior art use enzymes to cleave different linkages. For example, lysozyme has been used to hydrolyze the N-acetylglucosamine/N-acetylmuramic acid polymer. Mutanolysin has been used to hydrolyze the linkage between the N-acetylglucosamine/N-acetylmuramic acid polymer and the peptide portion, and lysostaphin has been used to hydrolyze the peptide portion of the bacterial cell wall.

The absolute molar mass distributions of the capsular polysaccharides of this invention is narrow as indicated by low polydispersity values ($M_W/M_N$) (see Table 2). This uniformity is valuable for producing consistent and effective vaccine products.

C. Vaccines

This invention is also directed to vaccine preparations. According to this invention, the isolated CPS described above may be used as an antigen to generate antibodies that are reactive against the CPS and hence reactive against the organism from which the CPS was isolated.

The vaccines of this invention may provide active or passive immunity. Vaccines for providing active immunity comprise a purified CPS of this invention. Preferably, this vaccine comprises CPS conjugated to at least one antigenic peptide.

1. Antibodies

The techniques for CPS extraction and isolation, described above, provide for the production of abundant amounts of the CPS of this invention. This facilitates the generation of antibodies reactive against the CPS.

In another embodiment, antibodies directed against the CPS may be generated by any of the techniques that are well known in the art. According to one approach, the antibodies may be generated by administering an isolated CPS preparation or derivatives or fragments thereof into a host animal. The host animal may be, but is not limited to, rat, mouse, rabbit, non-human primate, or a human. Preferably, the host is human. Immunological responses may be increased by the use of adjuvants which are known in the art.

Monoclonal antibodies directed against the CPS may also be prepared by any of the techniques that are well known in the art. According to one method, cultures of hybridoma cell lines are used (Kohler and Milstein (1975) *Nature* 256:495–497). Monoclonal antibodies directed against the CPS may be human monoclonal antibodies, chimeric monoclonal antibodies or humanized monoclonal antibodies made by any of the techniques that are well known in the art. According to one approach, chimeric monoclonal antibodies may be generated that have a non-human (e.g. mouse) antigen-binding domain combined with a human constant region. (Takeda et al. (1985) *Nature* 314:452). Humanized antibodies can be generated according to the procedures of Queen et al., U.S. Pat. No. 5,585, 089.

Antibodies directed against the CPS may be purified by any of the techniques that are well known in the art including, but not limited to immunoabsorption or immunoaffinity chromatography, or other chromatographic methods (e.g. HPLC). Antibodies may also be purified as immunoglobulin fractions from serum, plasma or cell culture medium.

Antibody molecules of this invention may be intact immunoglobulin molecules, substantially intact immunoglobulin molecules, or those portions of an immunoglobulin molecule, for example Fab fragments, that contain the antigen binding site.

Fragments of antibodies directed against the CPS may be generated by any of the techniques that are well known in the art. (Campbell (1985) *Laboratory Techniques in Biochemistry and Molecular Biology*, Vol. 13, Burdon, et al. (eds.), Elsevier Science Publishers, Amsterdam).

2. Conjugate molecules

The CPS of this invention may be used to elicit antibody responses to a variety of gram-negative and gram-positive bacteria in an individual either alone or when conjugated to another immunogenic molecule such as a polypeptide or protein. Conjugation of the CPS to the polypeptide converts the immune response to the CPS which is typically T-cell independent to one which is T-cell dependent. Accordingly, the size of the polypeptide is preferably one which is sufficient to cause the conversion of the response from T-cell independent to T-cell dependent. It may by useful to use smaller polypeptides for the purpose of providing a second immunogen.

Any mode of conjugation may be employed to conjugate the CPS component with the peptide. A preferred method is that described in U.S. Pat. No. 4,356,170 which describes introducing terminal aldehyde groups into the polysaccharide via oxidative cleavage of vicinal diols, and coupling the aldehyde groups to the peptide amino groups by reductive amination.

It is to be understood, however, the conjugate vaccines of the invention are not limited to those produced via reductive amination. Thus, the vaccines may also be produced by conjugating the CPS with a peptide using any linking method known to those skill in the art such as an adipic dihydrazide spacer, as described by Schneerson, R. et al. (1980) *J. Exp. Med.* 1952:361–476, and in U.S. Pat. No. 4,644,059, or, for example, binary spacer technology as described by Marburg, S. et al. (1986) *J. Am. Chem. Soc.* 108:5282–5287.

This invention provides the ability to produce conjugate molecules wherein the peptide is linked to the CPS through one or more sites on the CPS. Accordingly, conjugate molecules prepared according to this invention, with respect to the protein component, may be monomers, dimers, trimers and more highly cross-linked molecules wherein the CPS cross-links together multiple proteins.

In another embodiment of this invention, antibodies directed against the CPS of this invention may be used as a pharmaceutical preparation in a therapeutic or prophylactic application in order to confer passive immunity from a host individual to another individual (i.e., to augment an individual's immune response against gram-negative or gram-positive bacteria or to provide a response in immuno-compromised or immuno-depleted individuals including AIDS patients). Passive transfer of antibodies is known in the art and may be accomplished by any of the known methods. According to one method, antibodies directed against the CPS or conjugates thereof of this invention are generated in an immunocompetent host ("donor") animal, harvested from the host animal, and transfused into a recipient individual. For example, a human donor may be used to generate antibodies reactive against the CPS or CPS conjugate of this invention. The antibodies may then be administered in therapeutically or prophylactically effective amounts to a human recipient in need of treatment, thereby conferring resistance in the recipient against bacteria which are bound by antibodies elicited by the polysaccharide component. (See Grossman, M. and Cohen, S. N., in "Basic and Clinical Immunology", 7th Ed., (Stites, D. P. and Terr, A. T. eds., Appleton & Lange 1991) Chapter 58 "Immunization".)

3. Pharmaceutical compositions

The pharmaceutical compositions of this invention may comprise the CPS or conjugated molecules comprising CPS and pharmacologically acceptable carriers such as saline, dextrose, glycerol, ethanol or the like. In another embodiment the pharmaceutical composition comprises another immunogenic moiety, such as a peptide, or compositions comprising antibodies elicited by one of the CPS of this invention. The composition may also comprise adjuvants to enhance the immunological response of the recipient. Such adjuvants may be aluminum based such as alum or long chain alkyl adjuvants such as stearyl tyrosine (see U.S. Ser. No. 583,372, filed 9/17/90; European Patent, EP 0 549 617 B1; Moloney et al. U.S. Pat. No. 4,258,029). See also Jennings, et al. U.S Pat. No. 5,683,699 and Paoletti, et al. *J. Infectious Diseases* 1997; 175:1237–9. These pharmaceutical compositions are particularly useful as vaccines.

For eliciting passive immunity, the pharmaceutical composition may be comprised of polyclonal antibodies or monoclonal antibodies or their derivatives or fragments thereof as described above. The amount of antibody, fragment or derivative will be a therapeutically or prophylactically effective amount as determined by standard clinical techniques.

The pharmaceutical preparations of this invention may be introduced to an individual by methods known to be effective in the art. Intradermal, intraperitoneal, intravenous, subcutaneous, intramuscular, oral and intranasal are among, but not the only, routes of introduction.

The compositions of the invention may comprise standard carriers, buffers or preservatives known to those in the art which are suitable for vaccines including, but not limited to, any suitable pharmaceutically acceptable carrier, such as physiological saline or other injectable liquids. Additives customary in vaccines may also be present, for example stabilizers such as lactose or sorbitol and adjuvants to enhance the immunogenic response such as aluminum phosphate, hydroxide, or sulphate and stearyl tyrosine. The vaccines produced according to this invention may also be used as components of multivalent vaccines which elicit an immune response against a plurality of infectious agents.

Vaccines of the present invention are administered in amounts sufficient to elicit production of antibodies as part of an immunogenic response. Dosages may be adjusted based on the size, weight or age of the individual receiving the vaccine. The antibody response in an individual can be monitored by assaying for antibody titer or bactericidal activity and boosted if necessary to enhance the response. Typically, a single dose for an infant is about 10 μg of conjugate vaccine per dose or about 0.5 μg-20 pg/kilogram. Adults receive a dose of about 0.5 μg–20 μg/kilogram of the conjugate vaccine. For the CPS vaccine, a typical dose is about 25 μg of each individual CPS per dose. That is, a vaccine against group B streptococcus could comprise 25 μg of each of the CPS form each of the nine serotypes.

D. Diagnostic kits

In another embodiment, the CPS of this invention or derivatives or fragments thereof may be used to produce safer diagnostic kits that do not incorporate toxins such as pneumolysis toxin but can still indicate the presence of antibodies directed against gram-negative or gram-positive bacteria. The presence of such antibodies can indicate prior exposure to the pathogen, and predict individuals who may be resistant to infection. The diagnostic kit may comprise at least one of the CPS of this invention or derivatives or fragments thereof and suitable reagents for the detection of an antibody reaction when the modified CPS or derivatives or fragments are mixed with a sample that contains antibody directed against gram-negative or gram-positive bacteria. An antibody reaction may be identified by any of the methods described in the art, including but not limited to an ELISA assay. Such knowledge is important, and can avoid unnecessary vaccination.

Alternatively, the diagnostic kit may further comprise a solid support or magnetic bead or plastic matrix and at least one of the CPS of this invention or derivatives or fragments thereof.

In some cases, it may be preferred that the CPS or derivatives or fragments are labeled. Labeling agents are well-known in the art. For example, labeling agents include but are not limited to radioactivity, chemiluminescence, bioluminescence, luminescence, or other identifying "tags" for convenient analysis. Body fluids or tissues samples (e.g. blood, serum, saliva) may be collected and purified and applied to the diagnostic kit. The CPS, derivatives or fragments may be purified or non-purified and may be composed of a cocktail of molecules.

Solid matrices are known in the art and are available, and include, but are not limited to polystyrene, polyethylene, polypropylene, polycarbonate, or any solid plastic material in the shape of test tubes, beads, microparticles, dip-sticks, plates or the like. Additionally matrices include, but are not limited to membranes, 96-well micro titer plates, test tubes and Eppendorf tubes. In general such matrices comprise any surface wherein a ligand-binding agent can be attached or a surface which itself provides a ligand attachment site.

All publications, patents and articles referred to herein are expressly incorporated herein in toto by reference thereto. The following examples are presented to illustrate the present invention but are in no way to be construed as limitations on the scope of the invention. It will be recognized by those skilled in the art that numerous changes and substitutions may be made without departing from the spirit and purview of the invention.

EXAMPLES

A. Bacteria Strains, Growth Media, and Cultivation Conditions

Type Ib group B streptococcal strain H36b (ATCC 12401) was obtained from American Type Culture Collection (Rockville, Md.). The other strains used, 090 (type Ia), 18RS21 (type II), M781 (type III), and 1169-NT I (type V), were kindly provided by D. L. Kasper, Harvard Medical School. *Neisseria meningitidis* types B, C, Y and WI 35 were kindly provided by Carl Frasch at CBER, FDA and *Escherichia coli* K1 was kindly provided by Willie Vann at CBER, FDA.

Each of the group B streptococcal strains was grown individually in a dialysate (10,000 nominal molecular weight limit (NMWL) membrane), Pellicon cassette system (Millipore Corp., Bedford, Mass.) of 3.5% Columbia broth (Difco Laboratories, Inc., Detroit, Mich.) supplemented with 6% glucose. A 150 mL seed culture grown for 8 h in a shaking Erlenmeyer flask at 37° C. was used to inoculate a Bioflo IV 20-liter fermentor (New Brunswick Scientific Co., Edison, N.J.) filled with 14 liters of broth (vide supra). The fermentation culture was maintained at 37° C., continually adjusted to pH 7.1 with the addition of 10 N NaOH and aerated at 1.5 l/min. The cells were harvested after 17 h by microfiltration through a MiniKros 0.2 μm porosity, hollow-fiber cartridge (Microgon, Inc., Laguna Hills, Calif.). The culture supernatant was sterilely maintained at 4° C. until further processed. Final cell pellets were obtained by centrifugation of separated cells at 9000 rpm in a Sorvall GSA rotor (DuPont Clinical & Instruments Div., Wilmington, Del.) for 50 min.

B. General Method for Producing Capsular Polysaccharides

1. Extraction and hydrophobic-interaction chromatography

Pellets were suspended in four volumes of 1 N NaOH using the gram wet weight of the cell paste as one volume. The suspension was incubated at 37° C. overnight. Cell debris was removed by centrifugation for 30 min at 12,000 rpm in a Sorvall GSA rotor. After neutralization with concentrated HCl (J. T. Baker, Phillipsburg, N.J.), the supernatant was diafiltered against 2 N NaHCO$_3$ (pH 9.6) using a Pellicon 10,000 NMWL membrane. The resulting retentate was then loaded onto a Pharmacia XK 26/60 column packed with Phenyl Sepharose HP (Pharmacia Biotech; Piscataway, N.J.), pre-equilibrated with 2 N NaHCO$_3$, using the Pharmacia preparative chromatography system described below. The column was first eluted at 4 ml/min with one column volume of 2 N NaHCO$_3$ followed by two column volumes of water. Fractions were assayed for polysaccharide (vide infra) and those containing capsular polysaccharide were pooled.

Capsular polysaccharides were also purified from culture supernatants. After removal of cells, the broth was concentrated 10–15 fold (Pellicon, using 10,000 NMWL membrane) and diafiltered against 10 volumes of water. To the resulting retentate was added 10 N NaOH to a final concentration of 1 M. This solution was incubated at 37° C. overnight and neutralized with concentrated HCl. Processing continued as described above for the cell extraction.

For one batch of type III capsular polysaccharide, cells and culture supernatant were extracted together, as follows. Culture supernatant, separated from cells, was concentrated and diafiltered, and the resulting retentate treated with base as described above. Cell pellet was suspended in four volumes of the base-treated retentate, and further processed as described above for cell extraction (vide supra).

2. Re-N-acetylation

Because the exposure of the polysaccharide to the previously described extraction conditions releases N-acetyl groups from the polysaccharides, the polysaccharides were re-N-acetylated by the dropwise addition of acetic anhydride (Aldrich Chemical Co., Milwaukee, Wis.) to the pooled fractions to a final concentration of 0.8 M. This reaction mixture was stirred at room temperature for 1 h and maintained at pH 9 with the addition of 10 N NaOH. The reaction pH was then increased to 13, and the reaction was continued for an additional 30 min. The solution containing re-N-acetylated capsular polysaccharide was diafiltered against water using a Minitan cassette system (10,000 NMWL membrane, Millipore) and the retentate lyophilized. The lyophil was redissolved in PBS (pH 7.4) and purified by gel-permeation chromatography on Superdex 200 PG (vida infra). Fractions containing capsular polysaccharide were pooled, diafiltered against water (vida supra) and the retentate lyophilized to yield purified CPS.

3. Gel-permeation chromatography

Analytical gel-permeation chromatography (GPC) was done on a Pharmacia FPLC system equipped with a Pharmacia UV-1 ultraviolet detector (with 280-nm filter), a Waters Corp. (Milford, Mass.) R401 differential refractometer, and a Pharmacia Superose 6 HR 10/30 (highly cross-linked beaded agarose) column. The column was eluted at 0.5 ml/min with PBS, pH 7.4. Dextran (approx. mol wt 2×10$^6$; Sigma Chem Co., St. Louis, Mo.) was used to determine the void volume ($V_o$) and sodium azide was used to determine the total bed volume ($V_t$). Relative elution volumes are expressed as $K_{av}=(V_e-V_o)/(V_t-V_o)$, in which $V_e$ is elution volume from the RI profile. Preparative GPC was done on a Pharmacia system comprising the above mentioned detectors, a P-50 pump, a FRAC-100 fraction collector, a GP-250 Plus controller, and an XK 26/100 column packed with Superdex 200 PG (Pharmacia). The column was eluted with PBS at 1 ml/min.

C. Analysis of Polysaccharides

1. Molar mass determination

Absolute molar mass distributions of polysaccharides were determined by analytical GPC with detection by in-line multiangle laser-light-scattering photometry and differential refractometry (GPC-MALLS/RI). This method was performed on a liquid chromatography system consisting of a Jasco PU-980 HPLC pump (Easton, Md.), a Rheodyne model 7125 injection valve (Cotati, Calif.), and a Superose 6 HR 10/30 column equilibrated with PBS and with a flow rate of 0.5 ml/min. The mobile phase was prepared in ultra-high-purity water (Stephens Scientific, Riverdale, N.J.) and filtered through a 25 mm diameter in-line filter (Millipore) equipped with a Millipore type GV 0.22-mm membrane. Polysaccharide samples (1–2 mg) were dissolved at a concentration of 10 mg/ml in the mobile phase, and the resulting solutions were centrifuged for 2 to 3 min at 14,000 rpm in a microcentrifuge to remove particulates before injection. Column effluents were directly analyzed with an in-line miniDAWN fixed-triple-angle laser-lightscattering photometer (Wyatt Technology Corp., Santa Barbara, Calif.) coupled to a Hewlett-Packard model 1047A differential refractometer. The analog signal output of the refractometer was connected to the miniDAWN through an auxiliary input channel. Light-scattering data was acquired and processed with Wyatt's ASTRette and EASI software. Peak area was calculated by the Wyatt software as the summation of the areas of 200–300 trapezoidal divisions, or "slices", over the full range of a peak. From the area thus obtained, the weight-average and number-average molar masses ($M_w$ and $M_n$, respectively) of a polysaccharide eluting in a given peak were calculated. The specific refractive-index increment (dn/dc) was determined for all polysaccharides to be 0.140 ml/g using the on-line HP 1047A refractometer. This value was comparable to values previously obtained for other polysaccharides (7,8,38).

2. NMR spectroscopy

One-dimensional $^1$H NMR spectra of polysaccharide samples (4–5 mg/ml) in D$_2$0 (Aldrich) were recorded at 500 MHz on a Bruker Instruments AMX 500 spectrometer (Billerica, Mass.). Spectral data were acquired at 50° C., and chemical shifts were referenced to external 2,2,3,3-tetradeuterio-3-(trimethylsilyl)propionate (Aldrich) in D$_2$0.

3. Chemical analyses

Polysaccharide content in preparative column effluents and in purified polysaccharides was determined by a modification of the microscale orcinol assay of Reuter and Schauer (35) for sialic acid. Briefly, 100 μl of sample or control, containing 1–1.5 μg of NeuAc standard or up to 300

μg/ml of purified capsular polysaccharide, was added to 100 μl orcinol reagent (35) in a 1.5 ml microcentrifuge tube. Samples were mixed well and heated in a boiling water bath for 15 min. After samples were cooled in watered ice for 5 min, 500 μl of isoamyl alcohol (Fluka Chemical Co., Ronkonkoma, N.Y.) was added to each sample. The sample was thoroughly mixed and centrifuged in a microcentrifuge at 3000 rpm for 2–3 min. This procedure was repeated to ensure complete extraction of the chromophore into the alcohol. A 200 μl portion from the alcoholic phase of each sample was transferred to a 96-well flat-bottom low binding polystyrene microliter plate (Coming Costar Corp., Cambridge, Mass.) and read at 560 nm in a Molecular Devices Emax microplate reader (Menlo Park, Calif.). Purity of final polysaccharide preparations was derived from sialic acid content using the following formula weights: 314.3 g/mol for terminal NeuAc residue; 1004 g/mol for repeat unit of type Ia, Ib, or III CPS; 1328 g/mol for repeat unit of type II or V CPS.

Protein content was determined for samples containing 1–2 mg capsular polysaccharide per ml in PBS by the Bradford procedure (9) using Pierce (Rockford, Ill.) Coomassie Plus reagent and horse IgG as standard. Nucleic acid content was determined by direct UV photometry at 260 nm. Photometric measurements for these assays were made with a Shimadzu model UV160U spectrophotometer (Shimadzu Scientific Inst., Columbia, Md.).

D. Yields

Yields of capsular polysaccharide obtained from the various group B streptococcal serotypes are shown in Table 1. For all serotypes, polysaccharide purified from cell pellets exceeded that from culture supernatants, ranging from 4-fold higher yield for type II to 60-fold more for type Ib. For comparison, yields from supernatant as well as from cells are given in Table I as milligrams of polysaccharide per liter of culture (mg/L). Thus, when 14-liter fermentations are considered, total yields from cells ranged from 1.1 g for type Ia to 0.6 g for type II, whereas total yields from supernatants ranged from 150 mg for type II to 14 mg for type Ib. When cells and supernatant from a type III fermentation were processed together, the yield, 63 mg/L or 0.9 g total, was similar to that obtained from the cell pellet alone. The variation among the group B streptococcal strains studied in the ratios of isolated yields of capsular polysaccharides from cells to those from supernatants is suggestive of the different tendencies among serotypes to release capsular polysaccharides under the present growth conditions. Quantities of cell-associated capsular polysaccharides purified by this procedure approach the amounts found available from batch fermentations of group B streptococcal strains of types Ia, III, IV, V, and VI, deducible from the levels of cell-bound sialic acid (used as a marker of capsular polysaccharides), as reported by von Hunoistein et al. (39). More robust extraction conditions (e.g., stronger base, higher temperature, or agitation of the extraction mixture) would be expected to improve the yields of cell-bound capsular polysaccharides.

TABLE 1

Yields of Group B Streptococcal Capsular Polysaccharide

| Serotype | Yield Supernatant (mg/L)[A] | Yield Cell Pellet (mg/L)[A] |
|---|---|---|
| Ia | 4 | 79 |
| Ib | 1 | 64 |
| II | 11 | 42 |
| III[B] | 4 | 65 |
| V | 5 | 65 |

[A]Yields are expressed as mg of final purified capsular polysaccharide per liter of growth culture.
[B]When broth and cells were processed together, type III group B streptococci yielded 63 mg/L.

Results

A. Analysis of Purified Polysaccharides

For each of the group B streptococcal serotypes studied, one-dimensional $^1$H NMR spectrometry of polysaccharide preparations from both sources confirmed their identity with previously published spectral data for the respective type polysaccharides (41,44). Moreover, the NMR spectra of all of these preparations indicated very low levels of contamination. Representative NMR spectra of the five group B streptococci polysaccharides are shown in FIGS. 1–5. Nucleic acid levels, as detected by direct uv photometry at 260 nm, did not exceed 1% by mass, whereas protein, as assayed by the Bradford method (9) was not detectable in any polysaccharide preparation above the lower limit of detection of this assay (1 μg/ml). Purities of all polysaccharides, calculated from their sialic acid content as estimated by a modified microscale orcinol assay (35), were about 100%. For all polysaccharide preparations obtained by the procedure described above, the spectral and photometric data are therefore consistent with highly purified capsular polysaccharides with minimal contamination by proteins or nucleic acids.

B. Molecular Size of Polysaccharides

The relative elution volumes (as $K_{AV}$) of the purified polysaccharides on Superose 6, taken from the peak maxima of their RI-detected GPC profiles, are given in Table 2.

In separate analyses, the absolute molar-mass distributions of the polysaccharides were determined by GPC-MALLS/RI. This method allows direct estimation of molar mass of macromolecules, independent of chromatographic parameters such as flow rate and retention volume, and without the necessity of secondary standards whose hydrodynamic properties may vary greatly from the analyte of interest. The utility of GPC-MALLS/R1 as a characterization method has been well established for polysaccharides of pharmaceutical interest (7,8,10,17,25). Molar-mass distributions are usually presented as the weight-average molar-mass ($M_W$) and the polydispersity ($M_W/M_N$), which is indicative of the breadth of a distribution. As the polydispersity approaches unity, the molar-mass distribution approaches homogeneity.

Molar-mass data for the purified group B streptococcal polysaccharides are given in Table 2. For each of the serotypes, the molar-mass distributions for polysaccharide preparations from both sources were similar. The weight-average molar masses of these preparations ranged from 92 kg/mol for the cell-associated capsular polysaccharides from type V to 318 kg/mol for the capsular polysacharrides of type Ia purified from culture supernatant. The distributions of all preparations were narrow, as indicated by their low polydispersity values ($M_W/M_N \leq 1.6$). These values were comparable to those obtained by similar analyses of capsular polysacharrides of several serotypes of *S. pneumoniae* and of *Haemophilus influenzae* type b (7,17).

TABLE 2

Biochemical and Biophysical Characterization of Purified Group B Streptococcal Capsular Polysaccharides

| Serotype | $K_{av}$ | $M_W$ (kg/mol)[A] | Polydispersity $M_W/M_n$ | Nucleic acid content (%) | Protein content (%) |
|---|---|---|---|---|---|
| Ia (S)[B] | 0.005 | 318 | 1.35 | 0.23 | 0.21 |
| Ia (C)[C] | 0.010 | 311 | 1.31 | 0.15 | <0.01 |
| Ib (S) | 0.191 | 170 | 1.20 | 0.95 | <0.01 |
| Ib (C) | 0.150 | 218 | 1.61 | 0.33 | <0.01 |
| II (S) | 0.152 | 246 | 1.46 | 0.13 | <0.01 |
| II (C) | 0.115 | 289 | 1.46 | 0.12 | <0.01 |
| III (S) | 0.343 | ND | ND | 0.58 | <0.01 |
| III (C) | 0.268 | 108 | 1.24 | 0.10 | <0.01 |
| III (S + C) | 0.272 | 104 | 1.22 | | |
| V (S) | 0.257 | 92 | 1.28 | 0.26 | 0.27 |
| V (C) | 0.156 | 179 | 1.15 | 0.17 | 0.09 |
| V (C) | 0.241 | 99 | 1.20 | | |

[A]Molar-mass data were determined by GPC-MALLS/RI
[B](S) denotes the polysaccharide was purified from supernatants
[C](C) denotes the polysaccharide was purified from cell pellets Considered with the NMR spectral data, the molar-mass distributions indicate that, for each serotype, differences between the polysaccharides purified from supernatants or cell pellets (as well as from both sources combined, for type III) are insignificant. Because the NMR spectra for the preparations for each serotype indicate that they are chemically identical, the immunochemical behavior of these preparations is also anticipated to be identical. Therefore, the decision whether to combine culture supernatant with cells for extraction is based only on the contribution to the yield expected from the supernatant (Table 1). It may therefore be preferable to use a combined extract of type II.

Immunochemical Analysis

A. Competitive Inhibition ELISA

Microtiter plates (NUNC Polysorp) were passively coated with either $GBSP_{Ia}$-HSA, $GBSP_{Ib}$-HSA, $GBSP_{II}$-HSA, $GBSP_{III}$-HSA, or $GBSP_V$-HSA, (100 ng of polysaccharide in 100 µL to each well) diluted in PBS (50 nM Sodium Phosphate, 150 mM NaCl, pH=7.4) for 1 h at 37° C. After the plates were washed with PBS +0.05% Tween 20 (PBS-Tween, pH=7.4), they were blocked with 150 µL/well of PBS +0.1% Bovine Serum Albumin. After the postcoat, the plates were washed again and stored at 4° C. until used.

Rabbit anti-whole cell Group B Streptococcus antisera directed against $GBSP_{Ia}$, $GBSP_{Ib}$, $GBSP_{II}$, and $GBSP_{III}$ (Dennis Kasper) were titrated separately on plates coated with $GBSP_{Ia}$-HSA, $GBSP_{Ib}$-HSA, $GBSP_{II}$-HSA, and $GBSP_{III}$-HSA, respectively. Similarly, rabbit anti-$GBSP_V$-TT antiserum was titrated on a plate coated with $GBSP_V$-HSA. The dilution corresponding to approximately 50% of the maximal signal was chosen as appropriate for the inhibition studies.

The antisera were diluted in PBS-Tween. Inhibitors were diluted five-fold serially in buffer containing the diluted antisera. Next, 100 µL of these samples were added to wells of coated microtiter plates in duplicate and incubated at room temperature for 1 h. After being washed, 100 µL of goat anti-rabbit immunoglobulin-horseradish conjugate (Kirkegaard & Perry) diluted in PBS-Tween according to the manufacturer's instructions were added to each well. The plates were incubated at room temperature and then washed again. The 100 µL of TMB microwell substrate (cat. no. 50-76-04, Kirkegaard & Perry) were added to each well. The reaction was stopped after 5 min by the addition of 100 µL one-component stop solution (cat. no. 50-85-04, Kirkegaard & Perry), and the absorbance at 450 nm was read. Inhibition was determined as percentage of maximum signal achieved with diluted antiserum in the absence of any inhibitor.

B. Results

The binding inhibition curves for each specific GBS antiserum Ia, Ib, II, III, V with their homologous capsular PS antigens are represented on FIGS. 5–10, respectively. As evidenced by these curves, each PS antigen whether extracted from the culture supernatant, or the broth, had similar inhibiting properties indicating their antigenic equivalence. Thus, the procedure employed to generate these capsular polysaccharides does not affect their antigenicity.

REFERENCES

1. Anderson, P., G. Peter, R. B. Johnson, L. H. Wetterlow and D. H. Smith. 1972. Immunization of humans with polyribophosphate, the capsular antigen of Haemophilus influenzae type b. J.Clin.Invest. 51:39–44.
2. Avery, O. T. and W. F. Goebel. 1931. Chemo-immunological studies on conjugated carbohydrate-proteins V. The immunological specificity of an antigen prepared by combining the capsular polysaccharide of type 3 pneumococcus with foreign protein. J.Exp.Med. 54:437–447.
3. Baker, C. J. and D. L. Kasper. 1985. Group B streptococcal vaccines. Rev.Inf.Dis. 7:458–467.
4. Baker, C. J., M. A. Rench, M. S. Edwards, R. J. Carpenter, B. M. Hays and D. L. Kasper. 1988. Immunization of pregnant women with a polysaccharide vaccine of group B Streptococcus. N.Engl.J.Med. 319:1180–1185.
5. Baker, C. J., M. A. Rench and D. L. Kasper. 1990. Response to Type III polysaccharide in women whose infants have had invasive Group B streptococcal infection. New Engl.J.Med. 322:1857–1860.
6. Baltimore, R. S., D. L. Kasper and J. Vecchitto. 1979. Mouse protection test for group B Streptococcus type III. J.Infect.Dis. 140:81–86.
7. Bednar, B. and J. P. Hennessey. 1993. Molecular size analysis of capsular polysaccharide preparations from *Streptococcus pneumoniae*. Carbohyd.Res. 243:115–130.
8. Beri, R. G., J. Walker, E. T. Reese and J. E. Rollings. 1993. Characterization of chitosans via coupled size-exclusion chromatography and multiple-angle laser light-scattering technique. Carbohyd.Res. 238:11–26.
9. Bradford, M. M. 1976. A Rapid and sensitive method for the quantitation of microgram quantities of protein utilizing the principle of protein-dye binding. Analyt.Biochem. 72:248–254.
10. D'mbra, A. J., J. E. Baugher, P. E. Concannon, R. A. Pon and F. Michon. 1997. Direct and indirect methods for molar-mass analysis of fragments of the capsular polysaccharide of *Haemophilus influenzae* type b. Anal.Biochem. (In Press)
11. Dick, W. E., Jr. and M. Beurret. 1989. Glycoconjugates of bacterial carbohydrate antigens. p. 48–114. In: J. M. Cruse and R. E. Lewis,Jr., Contributions to microbiology and immunology. S.Karger, Basel.
12. Dillon, H. C., Jr., S. Khare and B. M. Gray. 1987. Group B streptococcal carriage and disease: A 6-year prospective study. J.Pediat. 110:31–36.
13. Goebel, W. F. and O. T. Avery. 1931. Chemo-immunological studies on conjugated carbohydrate-proteins IV. The synthesis of the p-aminobenzyl ether of the soluble specific substance of type 3 pneumococcus and its coupling with protein. J.Exp.Med. 54:431–436.
14. Gold, R., M. L. Lepow, I. Goldschneider, T. L. Draper and E. C. Gotschlich. 1975. Clinical evaluation of group A and group C meningococcal polysaccharide vaccines in infants. J.Clin.Invest. 56:1536–1547.
15. Gold, R., M. L. Lepow, I. Goldschneider and E. C. Gotschlich. 1977. Immune response of human infants to polysaccharide vaccines of Groups A and C *Neisseria meningitidis*. J.Infect.Dis. 136S:S31–S35.
16. Gold, R. M., M. L. Lepow, I. Goldschneider, T. F. Draper and E. C. Gotschlich. 1978. Antibody responses of human infants to three doses of group A *Neisseria meningitidis* vaccine administered at two, four and six months of age. J.Infect.Dis. 138:731–735.
17. Hennessey, J. P., B. Bednar and V. Manam. 1993. Molecular size analysis of *Haemophilus influenzae* type b capsular polysaccharide. J.Liq.Chromat. 16:1715–1729.
18. Howard, J. G., G. H. Christie, B. M. Courtenay, E. Leuchars and A. J. S. Davies. 1971. Studies on immunological paralysis. VI. Thymic-independence of tolerance and immunity to type III pneumococcal polysaccharide. Cell.Immunol. 2:614–626.
19. Jennings, H. J., E. Katzenellenbogen, C. Lugowski and D. L. Kasper. 1983. Structure of the native polysaccharide antigens of type Ia and type Ib Group B Streptococcus. Biochemistry 22:1258–1263.
20. Jennings, H. J., K. -.G. Rosell and D. L. Kasper. 1980. Structural determination and serology of the native polysaccharide antigen of type III group B Streptococcus. Can.J.Biochem. 58:112–120.
21. Jennings, H. J., K. -.G. Rosell and D. L. Kasper. 1980. Structure and serology of the native polysaccharide antigen of type Ia group B Streptococcus. Proc.Nat.Acad.Sci.USA. 77:2931–2935.
22. Jennings, H. J., K. -.G. Rosell, E. Katzenellenbogen and D. L. Kasper. 1983. Structural determination of the capsular polysaccharide antigen of type II Group B Streptococcus. J.Biol.Chem. 258:1793–1798.
23. Jennings, H. J. and R. K. Sood. 1994. Synthetic glycoconjugates as human vaccines. p. 325–371. In: Y. C. Lee and R. T. Lee, Neoglycoconjugates: Preparation and applications. Academic Press, New York.
24. Kasper, D. L., C. J. Baker, R. S. Baltimore, J. H. Crabb, G. Schiffman and H.J. Jennings. 1979. Immunodeterminant specificity of human immunity to type III group B Streptococcus. J.Exp.Med. 149:327–339.
25. Knobloch, J. E. and P. N. Shaklee. 1997. Absolute molecular weight of low-molecular-weight heparins by size-exclusion chromatography with multiangle laser light scattering detection. Anal.Biochem. 245:231–241.
26. Lancefield, R. C. 1933. A serological differentiation of human and other groups of haemolytic streptococci. J.Exp.Med. 57:571–595.
27. Lancefield, R. C. 1938. A micro-precipitin technique for classifying hemolytic streptococci and improved methods for producing antigen. Proc.Soc.Exp.Biol.and Med. 38:473–478.
28. Lancefield, R. C., M. McCarty and W. N. Everly. 1975. Multiple mouse-protective antibodies directed against group B streptococci: Special reference to antibodies effective against protein antigens. J.Exp.Med. 142:165–179.
29. Madoff, L. C., L. C. Paoletti, J. Y. Tai and D. L. Kasper. 1994. Maternal immunization of mice with Group B streptococcal type III polysaccharide-beta C protein conjugate elicits protective antibody to multiple serotypes. J.Clin.Invest. 94:286–292.
30. Marques, M. B., D. L. Kasper, A. Shroff, F. Michon, H. J. Jennings and M. R. Wessels. 1994. Functional activity of antibodies to the group B polysaccharide of group B streptococci elicited by a polysaccharide-protein conjugate vaccine. Infect.Immun. 62:1593–1599.
31. Makela, P. R. H., H. Peltola, H. Kayhty, et al. 1977. Polysaccharide vaccines of group A *Neisseria meningitidis* and *Haemophilus influenzae* type b: A field trial in Finland. J.Infect.Dis. 136:S43–50.
32. Michon, F., J. R. Brisson, A. Dell, D. L. Kasper and H. J. Jennings. 1988. Multiantennary group-specific polysaccharide of group B Streptococcus. Biochem. 27:5341–5351.
33. Peltola, A., H. Kayhty, A. Sivonen and P. R. H. Mäkelä. 1977. *Haemophilus influenzae* type b capsular polysaccharide vaccine in children: A double blind field study of 100,000 vaccines 3 months to 5 years of age in Finland. Pediatrics 60:730–737.
34. Peltola, H., P. R. H. Makela, H. Jousimies, et al. 1977. Clinical efficacy of meningococcal group A vaccine in children three months to five years of age. N.Engl.J.Med. 297:686–691.
35. Reuter, G. and R. Schauer. 1994. Determination of sialic acids. p. 168–199. In: W. J. Lennarz and G. W. Hart, Methods in Enzymology Vol. 230 Techniques in Glycobiology. Academic Press, New York.
36. Robbins, J. B. and R. Schneerson. 1990. Polysaccharide-protein conjugates: A new generation of vaccines. J.Infect.Dis. 161:821–832.
37. Smith, A. L. and J. Haas. 1991. Neonatal Bacterial Meningitis. p. 313–333. In: W. M. Scheld, R. J. Whitley and D. T. Durack, Infections of the Central Nervous System. Raven Press, Ltd., New York.
38. Tsunashima, T., K. Moro, B. Chu and T. -Y. Liu. 1978. Characterization of group C meningococcal polysaccharide by light-scattering spectroscopy. III. Determination of molecular weight, radius of gyration, and translational diffusional coefficient. Biopolymers 17:251–265.
39. von Hunolstein, C., L. Nicolini, S. D'Ascenzi, C. Volpe, G. Alfarone and G. Orefici. 1993. Sialic acid and biomass production by *Streptococcus agalactiae* under different growth conditions. Appl.Microbiol.Biotechnol. 38:458–462.
40. Wessels, M. R., W. J. Benedi, H. J. Jennings, F. Michon, J. L. DiFabio and D. L. Kasper. 1989. Isolation and characterization of type IV group B Streptococcus capsular polysaccharide. Infect.Immun. 57:1089–1094.
41. Wessels, M. R., J. L. DiFabio, V. J. Benedi, et al. 1991. Structural determination and immunochemical characterization of the type V group B Streptococcus capsular polysaccharide. J.Biol.Chem. 266:6714–6719.
42. Wessels, M. R., L.C. Paoletti, D. L. Kasper, et al. 1990. Immunogenicity in animals of a polysaccharide-protein conjugate vaccine against type III group B Streptococcus. J.Clin.Invest. 86:1428–1433.
43. Wessels, M. R., L.C. Paoletti, A. K. Rodewald, et al. 1993. Stimulation of protective antibodies against type Ia and Ib group B streptococci by a type Ia polysaccharide-tetanus toxoid conjugate vaccine. Infect.Immun. 61:4760–4766.
44. Wessels, M. R., V. Pozsgay, D. L. Kasper and H. J. Jennings. 1987. Structure and immunochemistry of an oligosaccharide repeating unit of the capsule polysaccharide of Type III Group B Streptococcus: A revised structure for the Type III Group B streptococcal polysaccharide antigen. J.Biol.Chem. 262:8262–8267.
45. Wyle, S. A., M. S. Artenstein, B. L. Brandt, et al. 1972. Immunologic response of man to group B meningococcal polysaccharide vaccines. J.Infect.Dis. 126:514–522.

We claim:

1. A method of purifying capsular polysaccharides from cellular components of gram-negative and gram-positive bacteria, wherein the cellular components include protein and/or nucleic acid, the method comprising contacting the cellular components with a base reagent to obtain a mixture wherein the pH of the mixture is between about 9 and 14, separating the capsular polysaccharides from the cellular components, and recovering the capsular polysaccharides substantially free of the other cellular components.

2. The method according to claim 1 wherein a percentage of N-acetyl groups present on the capsular polysaccharide are hydrolyzed during extraction and are then re-acylated such that the re-N-acylated capsular polysaccharide is cross reactive with the native capsular polysaccharide.

3. The method of extracting capsular polysaccharides from cellular components of gram-negative and gram-positive bacteria according to claim 1 further comprising the steps:
   (a) separating the capsular polysaccharide from the other cellular components by chromatography;
   (b) reacting the capsular polysaccharide from step (a) with an acylating agent;
   (c) purifying the capsular polysaccharide from step (b) by chromatography.

4. The method according to claim 1, wherein the pH of the mixture is about 12.

5. The method according to claim 3, wherein the capsular polysaccharide is derived from any bacterium of the genus Streptococci.

6. The method according to claim 3, wherein the capsular polysaccharide is derived from group B Streptococci.

7. The method according to claim 3, wherein the capsular polysaccharide is derived from group B Streptococci types Ia, Ib, II, III V, or VI or VIII.

8. The method according to claim 3, wherein the base reagent comprises an organic base.

9. The method according to claim 3, wherein the base reagent comprises an inorganic base.

10. The method according to claim 3, wherein the base reagent comprises NaOH, KOH or LiOH.

11. The method according to claim 3, wherein the separating by chromatography step is hydrophobic-interaction chromatography.

12. The method according to claim 3, wherein the acylating agent is acetic anhydride, acetyl chloride, pentafluorophenyl acetate or 4-nitrophenyl acetate.

13. The method according to claim 3, wherein the purifying the capsular polysaccharide by chromatography step is gel-permeation chromatography.

14. The method according to claim 3, wherein the base reagent comprises an inorganic base, the separating by chromatography step is hydrophobic chromatography, the acylation reagent is acetic anhydride, acetyl chloride, pentafluorophenyl acetate or 4-nitrophenyl acetate, and the purifying the capsular polysaccharide by chromatography step is gel-permeation chromatography.

15. The method according to claim 3, wherein the base reagent comprises NaOH, hydrophobic-interaction chromatography is used in step (b) to separate capsular polysaccharide from nucleic acid, the acylating agent is acetic anhydride and the capsular polysaccharide is recovered in step (c) by gel filtration chromatogaphy.

16. The method according to claim 3, wherein the capsular polysaccharide is derived from any bacterium of the genus Neisseria.

17. The method according to claim 3, wherein the capsular polysaccharide is derived from *N. meningitidis* type C.

18. The method according to claim 1, wherein the purified capsular polysaccharide contains less than about 1% by mass of nucleic acid and less than about 1 ug/ml protein.

19. A method of purifying capsular polysaccharide from cellular components including nucleic acid and/or protein of gram-negative and gram-positive bacteria, the method comprising contacting bacterial cells, homogenized bacterial cells, bacterial culture supernatant, or a mixture thereof with a base reagent to obtain basic conditions sufficient to hydrolyze base labile bonds, separating the capsular polysaccharide from the other cellular components, and recovering the capsular polysaccharide substantially free of the other cellular components.

20. The method according to claim 19, wherein the basic conditions are between about pH 9 and pH 14.

21. The method according to claim 19, wherein the capsular polysaccharide contains N-acetyl groups and wherein at least a portion of these N-acetyl groups are hydrolyzed by treatment with the base reagent.

22. The method according to claim 20, wherein the basic conditions are about pH 12.

23. The method according to claim 22, wherein the method comprises contacting bacterial cells with the base reagent.

24. The method according to claim 19, wherein the purified capsular polysaccharide contains less than about 1% by mass of nucleic acid and less than about 1 ug/ml protein.

25. The method according to claim 19, wherein the separating step is chromatographic separation.

26. The method according to claim 19, wherein the capsular polysaccharide is derived from any bacterium of the genus Neisseria.

27. The method according to claim 26, wherein the capsular polysaccharide is derived from *N. meningitidis* type C.

28. The method according to claim 19, wherein the capsular polysaccharide is derived from any bacterium of the genus Streptococci.

29. The method according to claim 28, wherein the capsular polysaccharide is derived from group B Streptococci.

30. The method according to claim 29, wherein the bacteria are group B Streptococci types Ia, Ib, II, III V, VI or VIII.

31. A method of producing a group C meningococcal polysaccharide conjugate vaccine comprising (a) contacting group C meningococcal bacterial cells, homogenized bacterial cells, bacterial culture supernatant, or a mixture thereof comprising a group C meningococcal capsular polysaccharide with a base reagent to obtain basic conditions sufficiently basic to hydrolyze at least one N-acetyl group of the group C meningococcal polysaccharide, (b) separating the capsular polysaccharide from the product of step (a) and conjugating the polysaccharide to a polypeptide.

32. The method according to claim 31, wherein conjugation is accomplished by reductive amination.

33. The method according to claim 32, further comprising the steps of treating the de-N-acetylated polysaccharide with an acylating agent and treating the N-acylated polysaccharide with an oxidizing agent to oxidatively cleave vicinal diols to produce aldehyde groups.

34. The method according to claim 33, further comprising isolating the de-N-acetylated polysaccharide and isolating the re-acylated product.

35. The method according to claim 33, wherein the base reagent is selected from the group consisting of sodium hydroxide, potassium hydroxide and lithium hydroxide and the acylating agent is selected from the group consisting of acetic anhydride and acetyl chloride.

36. The method according to claim 1, wherein the pH of the mixture is sufficient to degrade nucleic acid.

37. The method according to claim 19 or 31, wherein the basic conditions are sufficient to degrade nucleic acid.

38. The method according to claim 1, 19, or 31, wherein the method is protease free.

39. The method according to claim 1, 19, or 31 wherein the method is nuclease free.

40. The method according to claim 1, wherein the method comprises contacting bacterial cells, homogenized bacterial cells, bacterial culture supernatant, or a mixture thereof with the base reagent.

* * * * *